United States Patent [19]
Wheeler et al.

[11] Patent Number: 5,939,577
[45] Date of Patent: Aug. 17, 1999

[54] METHOD FOR THE SYNTHESIS OF CHLOROSILANES

[75] Inventors: David R. Wheeler, Albuquerque, N.Mex.; Timothy P. Pollagi, Dayton, Ohio

[73] Assignee: Sandia Corporation, Livermore, Calif.

[21] Appl. No.: 09/120,964

[22] Filed: Jul. 22, 1998

[51] Int. Cl.[6] ....................................................... C07F 7/08
[52] U.S. Cl. ............................................ 556/477; 556/430
[58] Field of Search ...................................... 556/477, 430

[56] References Cited

U.S. PATENT DOCUMENTS

| | | | |
|---|---|---|---|
| 3,231,333 | 1/1966 | Jenkner | 556/477 |
| 5,258,535 | 11/1993 | Ishikawa et al. | 556/430 |

*Primary Examiner*—Paul F. Shaver
*Attorney, Agent, or Firm*—Donald A. Nissen

[57] ABSTRACT

A novel method for the synthesis of chlorinated or partially chlorinated organosilanes and organopolysilanes. The chlorination is effected by contacting an organosilanes or organopolysilanes with anhydrous $CuCl_2$ in a nonpolar alkane solvent, preferably pentane or hexadecane, without the use of a catalyst. Copper metal, which is easily filtered, is a reaction product. The filtrate containing the chlorinated organosilane or organopolysilane can be used directly as a reactant to produce, for example, aminoorganosilanes.

7 Claims, No Drawings

METHOD FOR THE SYNTHESIS OF CHLOROSILANES

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates to a novel method for the preparation of chlorosilanes from organosilanes and organopolysilanes. Further, the present invention provides a simpler route for the synthesis of useful aminosilanes.

Chlorosilanes, and particularly chlorodisilanes, provide a desirable starting material for the synthesis of aminosilanes which are used extensively as silylating reagents in thin layer resist imaging processes (TLI) used for extreme ultraviolet (EUV) lithography.

One approach to imaging a circuit pattern onto a substrate involves introducing silicon into the surface layer of a photoresist material after exposure, as described by Coopmans, et al. "DESIRE: A New Route to Submicron Optical Lithography", *Solid State Technology*, pp. 93–97, June 1987. In this process, a resist material that will react with silation reagents is coated onto a substrate or an intervening planarizing layer and a circuit pattern is produced on the resist material by a standard UV exposure. Various modifications to Coopmans original silylation process, as well as alternative methods of employing silicon-based chemistry in top surface imaging (TSI) processes have been disclosed. However, at some point in all the above described TSI processes the resist coated wafer is subjected to silylation, generally by an organodisilane and preferably by an aminodisilane, such as dimethylaminopentamethyldisilane (PMDS).

The aminosilanes and aminodisilanes useful for the TSI processes discussed above can be readily produced by reaction between a chlorosilane or chloropolysilane and a nitrogen containing compound such as an amine or ammonia. While there are numerous methods for preparing aminosilanes or aminopolysilanes from organohalosilanes known in the art, the preparation of organochlorosilanes starting materials from organosilanes can be difficult. Existing synthetic methods can be complicated, difficult to control, produce low yields, require complicated steps to separate byproducts, or require expensive starting materials.

Ishikawa et al. in U.S. Pat. No. 5,258,535 disclose a method for the synthesis of partially chlorinated organosilane or organopolysilanes. The method comprises the stepwise substitution of Cl for H on a Si atom by the use of $CuCl_2$ in the presence of a CuI catalyst. While the method of Ishikawa et al. is successful in producing partially chlorinated organosilane and organopolysilane compounds, it suffers from two distinct disadvantages; HCl, produced as a reaction byproduct, can react with the chlorinated organosilane product, and another reaction byproduct CuCl can be difficult to separate from the chlorinated organosilane product. In both cases the reaction byproducts produced by the method of Ishikawa et al. can affect both the quality and quantity of the desired chlorinated organosilane reaction product. Moreover, the synthesis of Ishikawa et al. requires the use of 2 equivalents of the $CuCl_2$ reactant for each Cl atom added to the organosilane.

What is needed is a synthetic method that offers the ability to produce partially chlorinated organosilane or organopolysilane materials and eliminates undesirable reaction byproducts which can affect either, or both, the quality and quantity

SUMMARY OF THE INVENTION

The present invention provides a novel method for the synthesis of chlorinated or partially chlorinated organosilanes and organopolysilanes. In contrast to the prior art method of Ishikawa et al., the method for chlorination of organosilanes or organopolysilanes disclosed here, comprises the step of reacting organosilanes or organopolysilanes with anhydrous $CuCl_2$ in a nonpolar alkane solvent, preferably pentane or hexadecane, without the use of a CuI catalyst. By carrying out the chlorination reaction in pentane metallic copper is produced as a byproduct, which is easy to filter. Moreover, there is direct conversion of the organosilane or organopolysilane to its chlorinated or partially chlorinated analog without the undesirable formation of HCl. Further in contrast to Ishikawa, this inventive method requires the use of only one-half an equivalent of the $CuCl_2$ reagent for each Cl atom substituted on the organosilane or organopolysilane material rather than the 2 equivalents needed by Ishikawa et al.

While the exact mechanism of the chlorination mechanism according to the inventive method is not known, it is believed to involve the production of radical species. Thus, while the use of oxygen (air) or radiation as an reaction initiator has been found to be particularly useful any method known in the art to generate radical species can be used.

DETAILED DESCRIPTION OF THE INVENTION

The novel method disclosed here for chlorinating or partially chlorinating organosilanes or organopolysilanes is characterized by the following general reaction scheme

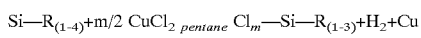

wherein $R_{(1-4)}$ can be H, methyl, ethyl, n-propyl, aryl such as phenyl, or Si—$R'_{(1-3)}$ and $R'_{(1-3)}$ can be methyl, ethyl, n-propyl, or aryl such as phenyl, and wherein at least one of $R_{(1-4)}$ or $R'_{(1-3)}$ is H. Moreover, in those cases wherein the starting silicon compound is an organopolysilane, the molecular structure is not limited to linear structures but can be branched or cyclic. In conducting the chlorination of organosilanes or organopolysilanes according to the inventive method, a catalyst is not required. However, it has been found that the use of oxygen (air) or ultraviolet (366 nm) radiation can be helpful in initiating the chlorination reaction.

The choice of a solvent or reaction medium for the inventive method is dependent on the ability of the solvent to sustain a radical initiated reaction. Thus, nonpolar alkane solvents, and particularly pentane and hexadecane, have been found to be desirable. The amount of solvent was not critical, however, a mole ratio of solvent to organosilane or organopolysilane of about 8–10:1 was desirable to provide efficient contact between the reactants.

To ensure the chlorination reaction proceeds smoothly it is preferable to keep the temperature of the solution in the range of about 10–20° C., particularly at the start of the chlorination reaction, which is characterized by the evolution of hydrogen gas and the appearance of a black solid phase which is finely divided copper metal.

In order to ensure successful chlorination according to the inventive method it is important to maintain anhydrous conditions. Only anhydrous reactants and solvent were employed and glassware was carefully dried before use.

In the event that oxygen (air) or ultraviolet radiation was used, either singly or in combination, to initiate the inventive chlorination reaction, they were applied until such time as the reaction started.

In order to make the method of the present invention clear it will be more fully described by the following examples. However, these examples are intended only to be illustrative of the invention and are not to be construed as limitations or restriction thereon, the invention being defined by the appended claims.

EXAMPLE 1

The inventive method was used to prepare 1,2-dimethylchlorodisilane from 1,2-dimethyldisilane.

A Claisen adapter and condenser were attached to a 50 ml round bottom flask, equipped with a stirring means and thermometer, and the whole assembly flame-dried. To the dried flask was added 0.392 g (2.92 mmol) $CuCl_2$ which was heated under vacuum until dry. The flask containing the anhydrous $CuCl_2$ was cooled to 15° C. and 5 ml of anhydrous pentane and 0.493 g (5.46 mmole) 1,2-dimethyldisilane were added. The solution was armed to about 18° C. and stirring commenced and dry air admitted until hydrogen evolution commenced. Simultaneously, copper metal, in the form of a black solid phase, was produced. Hydrogen evolution stopped after about 2 hrs and the solution was stirred for an additional 72 hrs. The copper precipitate was removed by filtering and NMR analysis of the filtrate showed 84% of the reaction product was the desired monochloride (1,2-dimethylchlorodisilane) and 16% was the dichloride (1,2-dichloro-1,2-dimethyldisilane). The results of HNMR (C6D12) analysis of the reaction product is given in Table 1 below.

TABLE 1

-0.05 ppm triplet 3H
0.30 ppm doublet 3H
3.6 ppm mult 2H
4.9 ppm mult 1H

EXAMPLE 2

An experimental procedure to prepare 1,2-dimethylchlorodisilane, similar to EXAMPLE 1, was carried out except here the reaction was initiated by ultraviolet radiation. The reaction mixture was irradiated with 366 nm light until the commencement of hydrogen evolution and the simultaneous appearance of the black copper metal precipitate. The solution was continuously stirred for 2 hours at which time the liquid phase was sampled. NMR analysis showed that 84% of the reaction product was 1,2 dimethylchlorodisilane and 16% was the dichloride.

EXAMPLE 3

The inventive method was used to prepare diethylchlorosilane from diethylsilane.

A reaction mixture was prepared as in EXAMPLE 1, except diethylsilane (0.470 g or 5.33 mmol) was substituted for 1,2 dimethyldisilane. Both ultraviolet radiation and oxygen (air) were used to initiate the reaction. At the end of 84 hrs of continuous stirring the precipitate had turned copper colored as a result of the formation of larger copper crystals which were easily filtered. NMR analysis of the filtrate showed that 86% of the diethylsilane had been converted to diethylchlorosilane.

EXAMPLE 4

An experiment similar to that of EXAMPLES 1 and 2 was performed except that here no initiator was employed and the reaction was started at 25° C. Shortly after the reaction had initiated, as indicated by the evolution of hydrogen, it was necessary to control the reaction rate by cooling to about 16° C. The reaction was stirred for an additional 24 hrs and the black copper solid phase filtered. A sample of the filtrate was analyzed and the analysis showed 78% conversion to the monochloride, 12% dichloride and the remainder, unreacted starting material.

The colorless filtrate, containing the 1,2 dimethylchlorodisilane reaction product, was then used to produce the desired dimethylaminodimethyldisilane by the following reaction scheme.

The filtrate was cooled to 0° C. under an inert atmosphere. An excess (slightly greater than 2 equivalents) of anhydrous dimethylamine was bubbled into the solution using a needle. The resulting heterogeneous mixture was stirred overnight under an atmosphere of dimethylamine. The mixture was then filtered under an inert atmosphere. The product was isolated by distillation at 105° C. with a 52% overall yield (based on dimethyldisilane). The HNMR (C6D12) analysis of the recovered product is given in Table 2.

TABLE 2

0.11 ppm triplet 3H
0.25 ppm doublet 3H
3.72 ppm mult 2H
4.85 ppm mult 1H

It should be noted that the precipitate produced by the method of the present invention is composed of very finely divided copper metal and, as such, is very pyrophoric and should be handled accordingly. As indicated in EXAMPLE 3 above, by continuing to stir the reaction mixture the copper metal particles will agglomerate into larger particles which are not only easier to filter but also present much less danger when separated from the solvent.

While the invention has now been described in terms of certain preferred embodiments, and exemplified with respect thereto, those skilled in the art will appreciate that various modifications, changes, substitutions, and omissions can be made without departing from the scope of the present invention which is limited only by the following claims.

We claim:

1. A method for the synthesis of chlorinated organosilanes and organopolysilanes, comprising reacting an organosilane or organopolysilane with anhydrous $CuCl_2$ in a solvent consisting essentially of a nonpolar alkane.

2. The method of claim 1, wherein the organosilanes and organopolysilanes are represented by the general formula Si—$R_{(1-4)}$, wherein $R_{(1-4)}$ can be H, methyl, ethyl, n-propyl, aryl such as phenyl, or Si—$R'_{(1-3)}$ and $R'_{(1-3)}$ can be methyl, ethyl, n-propyl, or aryl such as phenyl, and wherein at least one of $R_{(1-4)}$ or $R'_{(1-3)}$ is H.

3. The method of claim 1, further including the step of intiating the reaction with an initiator.

4. The method of claim 3, wherein the initiator is oxygen or light.

5. The method of claim 4, wherein the light is ultraviolet light.

6. The method of claim 5, wherein the ultraviolet light has a wavelength of 366 nm.

7. The method of claim 1, wherein the nonpolar alkane solvent is pentane or hexadecane.

* * * * *